United States Patent
Hill et al.

(10) Patent No.: US 7,058,447 B2
(45) Date of Patent: Jun. 6, 2006

(54) METHOD AND SYSTEM FOR DIRECTING BLOOD FLOW DURING A MEDICAL PROCEDURE

(75) Inventors: Michael R. S. Hill, Minneapolis, MN (US); Scott E. Jahns, Hudson, WI (US); James R. Keogh, Maplewood, MN (US)

(73) Assignee: Medtronic, Inc., Minneapolis, MN (US)

(*) Notice: Subject to any disclaimer, the term of this patent is extended or adjusted under 35 U.S.C. 154(b) by 0 days.

(21) Appl. No.: 10/421,537

(22) Filed: Apr. 23, 2003

(65) Prior Publication Data

US 2003/0216775 A1    Nov. 20, 2003

Related U.S. Application Data

(63) Continuation of application No. 09/670,370, filed on Sep. 26, 2000, now abandoned.

(51) Int. Cl.
*A61N 1/36* (2006.01)
*A61H 9/00* (2006.01)

(52) U.S. Cl. .......................... 607/3; 601/151

(58) Field of Classification Search ............ 601/6, 601/11, 148–152, 41, 43, 44, 84; 607/1–5, 607/9–10, 22, 24; 128/897–898; 600/481, 600/485, 505, 507
See application file for complete search history.

(56) References Cited

U.S. PATENT DOCUMENTS

| | | | | |
|---|---|---|---|---|
| 4,321,929 A | | 3/1982 | Lemelson et al. | 128/630 |
| 4,355,632 A | * | 10/1982 | Sandman | 601/152 |
| 4,753,226 A | * | 6/1988 | Zheng et al. | 601/150 |
| 5,007,893 A | | 4/1991 | Row | 600/20 |
| 5,199,428 A | | 4/1993 | Obel et al. | 607/44 |
| 5,218,954 A | * | 6/1993 | van Bemmelen | 601/151 |
| 5,531,776 A | | 7/1996 | Ward et al. | 607/105 |
| 5,800,334 A | | 9/1998 | Wilk | 600/18 |
| 5,971,911 A | | 10/1999 | Wilk | 600/18 |
| 6,007,559 A | | 12/1999 | Arkans | 606/201 |
| 6,213,960 B1 | | 4/2001 | Sherman et al. | 601/41 |

FOREIGN PATENT DOCUMENTS

| | | |
|---|---|---|
| EP | 0 440 111 A2 | 8/1991 |
| WO | WO 99/00057 | 1/1999 |
| WO | WO 00/01306 | 1/2000 |

* cited by examiner

*Primary Examiner*—Robert E. Pezzuto
*Assistant Examiner*—Kristen Mullen
(74) *Attorney, Agent, or Firm*—Michael Best & Friedrich LLP (57) ABSTRACT

A system of performing a medical procedure, such as surgery, is provided. The system comprises a compression member for compressing a body portion and a means for controlling the compression. Methods and devices for performing the medical procedure are also provided.

20 Claims, 4 Drawing Sheets

METHOD AND SYSTEM FOR DIRECTING BLOOD FLOW DURING A MEDICAL PROCEDURE

PRIORITY

This is a continuation of U.S. patent application Ser. No. 09/670,370, filed Sep. 26, 2000 now abandoned.

FIELD OF THE INVENTION

This invention relates to methods for performing a medical procedure, especially a procedure during which it is necessary to adjust the beating of the heart. More particularly, this invention relates to devices and systems for controlling blood flow while the beating of a heart is being modified in order to allow a medical procedure to be performed.

BACKGROUND OF THE INVENTION

The current leading cause of death in the United States is coronary artery disease in which the coronary arteries are blocked by atherosclerotic plaques or deposits of fat. The typical treatment to relieve a partially or fully blocked coronary artery is coronary artery bypass graph (CABG) surgery.

CABG surgery, also known as "heart bypass" surgery, generally entails using a graph to bypass the coronary obstruction. The procedure is generally lengthy, traumatic and subject to patient risks. Among the risk factors involved is the use of a cardiopulmonary bypass (CPB) circuit, also known as a "heart-lung machine," to pump blood and oxygenate the blood so that the patient's heart may be stopped during the surgery.

Conventional CABG procedures are typically conducted on a stopped heart while the patient is on a (CPB) circuit. A stopped heart and a CPB circuit enables a surgeon to work in a bloodless, still operative field. However, there are a number of problems associated with CABG procedures performed while on CPB including the initiation of a systemic inflammatory response due to interactions of blood elements with the artificial material surfaces of the CPB circuit and global myocardial ischemia due to cardioplegic cardiac arrest. For these reasons, avoiding the use of CPB or cardioplegic cardiac arrest may help minimize post-operative complications.

One method, as disclosed in U.S. Pat. No. 5,651,378 to inventors Matheny and Taylor and in U.S. Pat. No. 5,913,876 to inventors Taylor et al., for facilitating coronary bypass surgery on a beating heart and thereby avoid the use of CPB and cardioplegic cardiac arrest includes stimulating the vagal nerve electrically in order to temporarily stop or substantially reduce the beating of the heart. This may be followed by pacing the heart to start its beating.

Another method, as disclosed in two published PCT applications, WO 99/09971 and WO 99/09973, both to inventor Puskas, involves stopping the beating of the heart during coronary bypass surgery using electrical stimulation of the vagal nerve in combination with administration of drugs. Another method, as disclosed in U.S. Pat. No. 6,060,454 to inventor Duhaylongsod, involves stopping the beating of the heart during coronary bypass surgery via the local delivery of drugs to the heart.

Although it is desirable to stop the heart for a period of time in order to allow the surgeon to accomplish a required task without interference from heart movement, i.e. a motionless operative field, it is undesirable to have the heart stopped for too long a period of time since the body needs, among other things, a constant supply of oxygen. In fact, it is particularly important to maintain sufficient blood flow, and therefore oxygen flow, to the brain. Stopping the heart for prolonged periods of time may cause damage to the patient.

Once the heart is allowed to beat again, blood flows to the organs of the body. During a procedure, it is desirable to have the flow of blood directed toward the organs that most require oxygen, i.e. the brain. Compression of the extremities, such as the arms or legs, is one means to direct blood flow away from other organs that have less immediate need of oxygen during a medical procedure.

It would be desirable therefore to provide a method for controllably stopping or slowing the heart intermittently for diagnostic and therapeutic purposes.

Additionally, it would be desirable to provide a device for directing the flow of blood during a medical procedure.

Additionally, it would be desirable to provide a method for controllably directing the flow of blood to the areas most requiring oxygen during a medical procedure.

SUMMARY OF THE INVENTION

One aspect of the present invention provides a compression device for controlling blood flow during a medical procedure. The device includes a compression member that is positioned on a body portion and a control unit to activate compression of the compression member.

The device may include an opening to allow access to the body portion. The opening may be used to access a blood vessel to be harvested, such as a saphenous vein. The compression member of the device may cover the body or a limb of the patient. The device may also include a cardiac stimulator in communication with the control unit for stimulating a heart. The device may also include a nerve stimulator in communication with the control unit for stimulating a nerve.

Another aspect of the present invention provides a system for controlling blood flow to a target area during a medical procedure. The system includes a compression member that is positioned on a body portion. Compression of the compression member directs blood flow to the target area. The system also includes a control unit to activate compression of the body portion in synchronization with beating of a heart.

The system may also include a nerve stimulator in communication with the control unit to stimulate a nerve to stop beating of the heart. The nerve stimulator may be, for example, one or more electrodes, such as nerve stimulation electrodes, endotracheal electrodes, endoesophageal electrodes, intravascular electrodes, transcutaneous electrodes, intracutaneous electrodes, balloon-type electrodes, basket-type electrodes, umbrella-type electrodes, tape-type electrodes, suction-type electrodes, screw-type electrodes, barb-type electrodes, bipolar electrodes, monopolar electrodes, metal electrodes, wire electrodes, patch electrodes, cuff electrodes, clip electrodes, needle electrodes and probe electrodes. The nerve stimulator may stimulate a nerve such as a vagal nerve, a carotid sinus nerve, a fat pad.

The system may also include a cardiac stimulator in communication with the control unit to stimulate the heart in order to induce beating of the heart. The cardiac stimulator may be, for example, one or more electrodes, such as cardiac stimulation electrodes, clip electrodes, needle electrodes, probe electrodes, pacing electrodes, epicardial electrodes, patch electrodes, intravascular electrodes, balloon-type electrodes, basket-type electrodes, tape-type electrodes, umbrella-type electrodes, suction-type electrodes, endotracheal electrodes, endoesophageal electrodes, transcutaneous electrodes, intracutaneous electrodes, screw-type electrodes, barb-type electrodes, bipolar electrodes, monopolar electrodes, metal electrodes, wire electrodes and cuff electrodes.

The system may also include drug delivery means such as a spray, a cream, an ointment, a medicament, a pill, a patch, a catheter, a cannula, a needle and syringe, a pump, and an iontophoretic drug delivery device to deliver at least one drug during the procedure. The drug may be a beta-blocker, a cholinergic agent, a cholinesterase inhibitor, a calcium channel blocker, a sodium channel blocker, a potassium channel agent, adenosine, an adenosine receptor agonist, an adenosine deaminase inhibitor, dipyridamole, a monoamine oxidase inhibitor, digoxin, digitalis, lignocaine, a bradykinin agent, a serotoninergic agonist, an antiarrythmic agent, a cardiac glycoside, a local anesthetic, atropine, a calcium solution, an agent that promotes heart rate, an agent that promotes heart contractions, dopamine, a catecholamine, an inotrope glucagon, a hormone, forskolin, epinephrine, norepinephrine, thyroid hormone, a phosphodiesterase inhibitor, prostacyclin, prostaglandin and a methylxanthine. The drug may be naturally occurring or chemically synthesized.

The medical procedure may be a surgical procedure, a non-surgical procedure, a fluoroscopic procedure, a cardiac procedure, a vascular procedure, a neurosurgical procedure, an electrophysiological procedure, a diagnostic procedure, a therapeutic procedure, an ablation procedure, an endovascular procedure, a liver procedure, a spleen procedure, a pulmonary procedure, an aneurysm repair, an imaging procedure, a CAT scan procedure, a MRI procedure, a pharmacological therapy, a drug delivery procedure, a biological delivery procedure, a genetic therapy, a cellular therapy, a cancer therapy, a radiation therapy, a transplantation procedure, a coronary angioplasty procedure, a stent delivery procedure, an procedure, a procedure that requires precise control of cardiac motion, a procedure that requires precise control of bleeding, a non-invasive procedure, a minimally invasive procedure, an invasive procedure, a port-access procedure, an endoscopic procedure, a sternotomy procedure, a thoracotomy procedure and a robotic procedure.

Another aspect of the present invention provides method for restricting blood flow to a portion of the body during a medical procedure. A nerve is stimulated to reduce beating of a heart. The procedure is performed. Stimulation of the nerve is reduced to allow beating of the heart to occur. While the heart is beating, a portion of the body is compressed. Compression may be controlled based on blood flow. Stimulation of the nerve may also be stopped to allow beating of the heart to occur. The heart may also be stimulated stimulating the heart to induce beating. A vessel, such as a saphenous vein, may be harvested prior to compressing the body portion.

Another aspect of the present invention provides a method for directing blood flow to a target area during a medical procedure. A nerve is stimulated to reduce beating of the heart. The medical procedure is performed. Stimulation of the nerve is reduced or stopped. While the nerve stimulation is reduced, a body portion is compressed to direct blood flow from the body portion to the target area. The target area may be the brain. The body portion may be a limb. Compression may be controlled based on blood flow.

The foregoing, and other, features and advantages of the invention will become further apparent from the following detailed description of the presently preferred embodiments, read in conjunction with the accompanying drawings. The detailed description and drawings are merely illustrative of the invention rather than limiting, the scope of the invention being defined by the appended claims in equivalence thereof.

DETAILED DESCRIPTION OF THE PRESENTLY PREFERRED EMBODIMENTS

Figure 1:
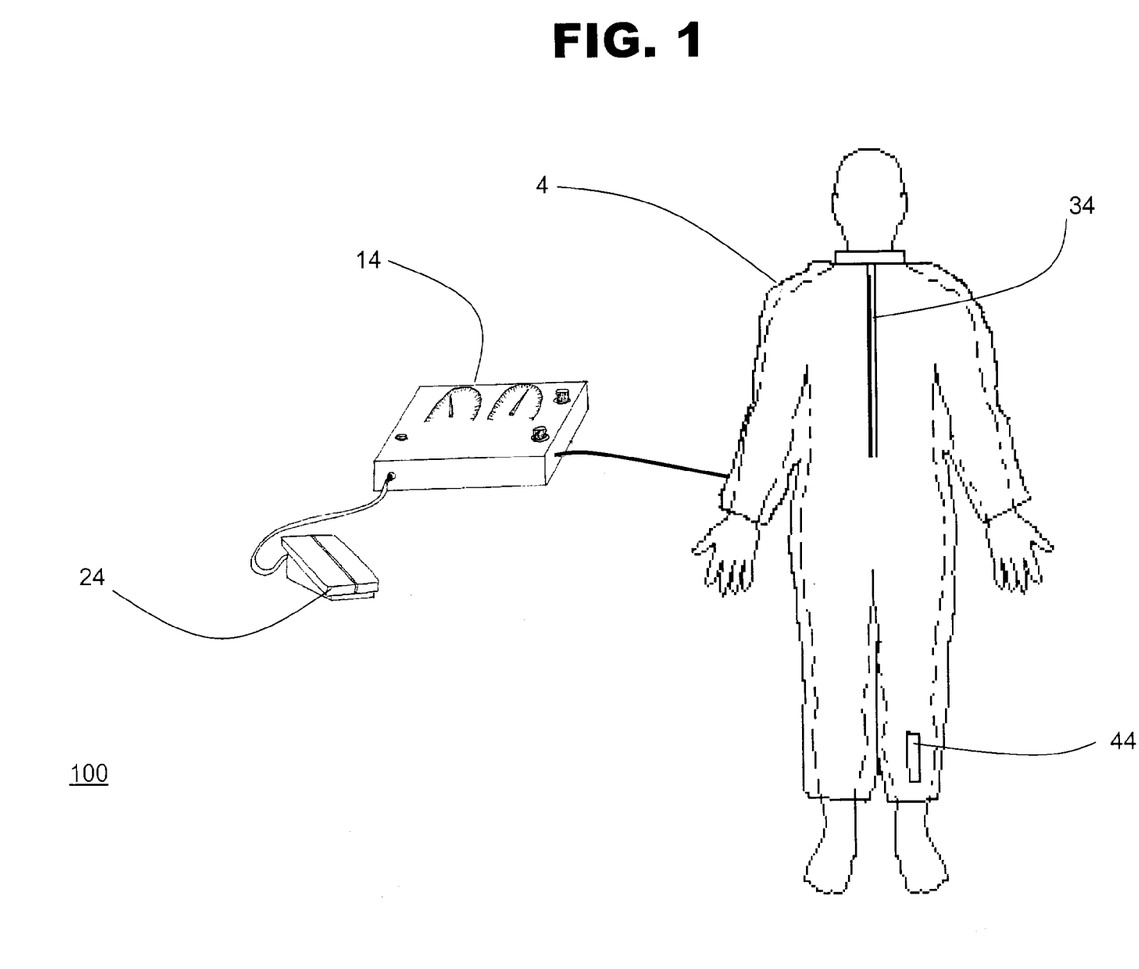
FIG. 1 is a schematic view of one embodiment of a system for directing blood flow during a medical procedure in accordance with the present invention.

FIG. 1 shows a schematic view of one embodiment of a system for performing a medical procedure in accordance with the present invention at 100. System 100 comprises a compression unit 4 and a control unit 14. As seen in FIG. 1, control unit 14 and compression unit 4 may be two separate components. Alternatively, control unit 14 may be integrated with compression unit 4. Control unit 14 may be detachably or permanently connected to compression unit 4.

As seen in FIG. 1, one embodiment of the compression unit 4 is a suit that may be fitted over the patient's body. The suit may be made of any suitable material for covering a patient such as, for example, polyurethane or plastic or fabric as is well known in the art. In one embodiment of the invention, compression unit 4 includes various means for accessing the patient such as a fastener 34 or openings 44 located strategically within the unit. For example, opening 44 may be used to access the patient in order to view or treat the limb being compressed. In one embodiment of the invention, opening 44 may be used to access a limb in order to harvest a vessel, such as the saphenous vein from the leg.

Additionally, the material of the compression unit 4 may be controllably inflated in such a manner that the parts of the patient within the compression unit may be compressed. In one embodiment, the amount and duration of compression is controlled by control unit 14. Additionally, the location or locations to be compressed by compression unit 4 may be controlled by control unit 14. For example, control unit 14 may be configured so that compression unit 4 compresses the arms and the legs covered by compression unit 4 at regular intervals. Alternatively, the patient's entire body may be compressed at regular intervals. Alternatively, a selected limb may be compressed at regular intervals. Alternatively, a user may controllably compress the compression unit 4 by using a control means associated with control unit 14. For example, in FIG. 1 a foot pedal 24 is shown which may be used to control compression of compression unit 4.

Additionally, the material of the compression unit 4 may be controllably cooled or warmed in such a manner that the parts of the patient within the compression unit may be cooled or warmed. In one embodiment, the amount and duration of cooling or warming is controlled by control unit 14. Additionally, the location or locations to be cooled or warmed by compression unit 4 may be controlled by control unit 14. For example, control unit 14 may be configured so that compression unit 4 cools or warms the arms and the legs covered by compression unit 4 at regular intervals. Alternatively, the patient's entire body may be cooled or warmed at regular intervals. Alternatively, a selected limb may be cooled or warmed at regular intervals. Alternatively, a user may controllably cool or warm the compression unit 4 by using a control means associated with control unit 14. In one embodiment of system 100, control unit 14 may provide output regarding the patient's condition or the condition of compression being administered. Alternatively, this output may be provided directly by compression unit 4. The surgeon may check this output periodically to see if the output reaches an appropriate level. Alternatively, system 100 may be programmed to indicate by a signal, such as an audio or visual signal, that compression is on or off or has reached a previously determined level.

All or a portion of compression unit 4 is placed in a manner that provides desired compression to the patient's body. Compression unit 4 may be attached in any suitable manner to the patient.

Figure 2:
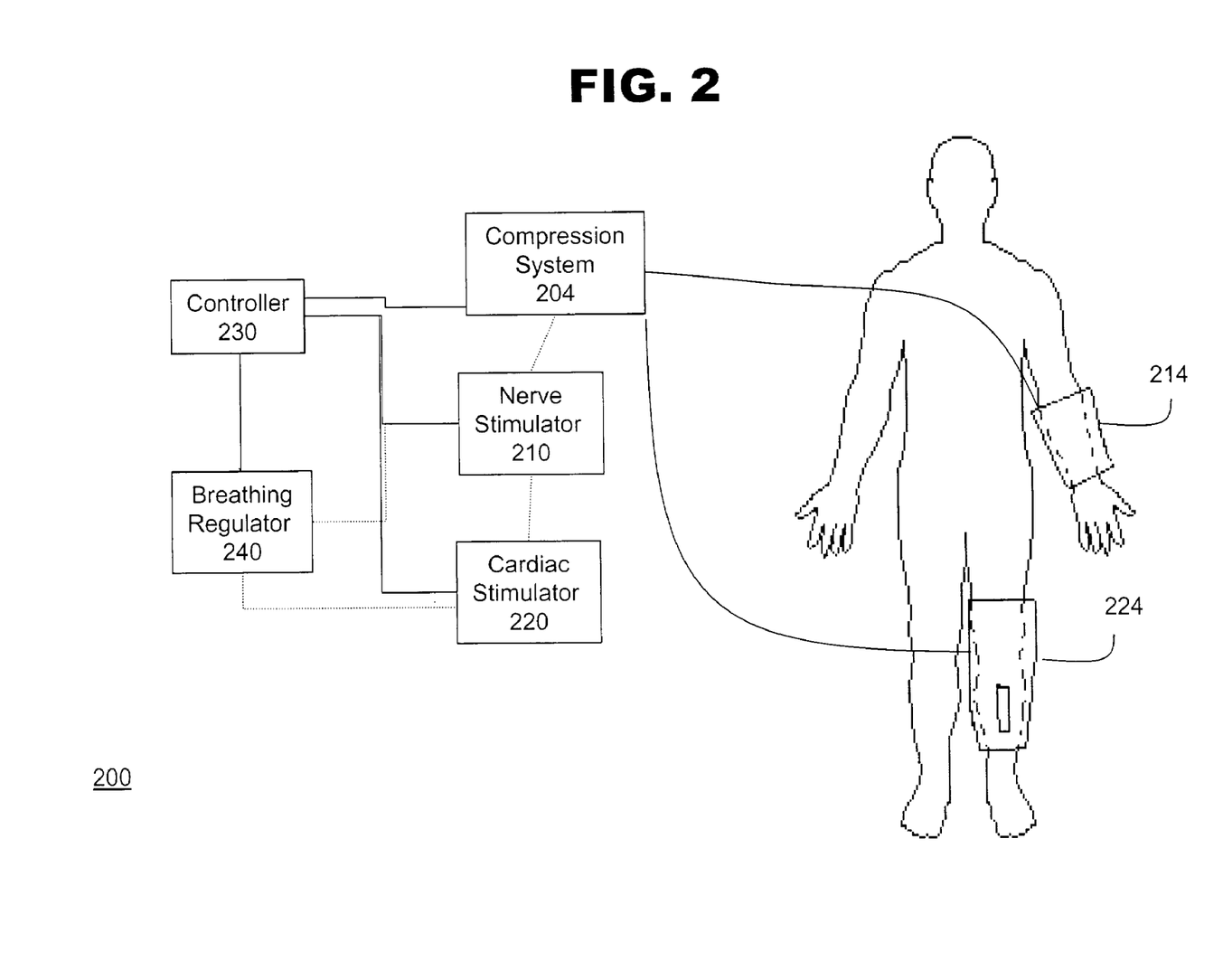
FIG. 2 is a schematic view of one embodiment of a medical system in accordance with the present invention.

FIG. 2 shows another embodiment of the present invention at 200. In this embodiment, compression unit 4 may be a sleeve or cuff 214, 224 that compresses an appropriate limb such as an arm sleeve 214 or leg cuff 224. As also seen in FIG. 2, any number or combination of compression units may be used to achieve the desired compression of the patient's body.

As seen in FIG. 2, one embodiment of the present invention may combine the compression system 100 with a controller 230 and/or other components. The controller may be used to coordinate the various elements, including the control portion 14 of the compression system 204 and the compression portion 4 of the compression system 204.

Compression system 204 may be any suitable system for controllably compressing portions of the patient's body. For example, compression system 204 may be system 100 as described above.

System 200 may also include a nerve stimulator 210. In one embodiment, the nerve stimulator 210 may be used to electrically manipulate cardiac rhythm by stimulating the vagus nerve. This vagal stimulation may produce asystole (slowing or stopping of the heart's beating.) Once this induced asystole is stopped, i.e. once the vagal stimulation is stopped, the heart may be allowed to return to its usual cardiac rhythm. Alternatively, the heart may be paced with an electrical pacing system, thereby maintaining a normal cardiac output. Vagal stimulation, alone or in combination with electrical pacing, may be used selectively and intermittently to allow a surgeon to perform a medical procedure during intermittent periods of asystole.

It is known that stimulation of the vagus nerve can reduce the sinus rate, as well as prolong AV conduction time or, if stimulation energies are high enough, induce AV node block. Use of vagal nerve stimulation to treat supraventricular arrhythmias and angina pectoris is disclosed in the article "Vagal Tuning" by Bilgutay et al., Journal of Thoracic and Cardiovascular Surgery, Vol. 56, No. 1, July, 1968, pp. 71–82. It is also known that stimulation of the carotid sinus nerve produces a similar result, as disclosed in the article "Carotid Sinus Nerve Stimulation in the Treatment of Angina Pectoris and Supraventricular Tachycardia" by Braunwald et al., published in California Medicine, Vol. 112, pp. 41–50, March, 1970.

As set forth in the article "Functional Anatomy of the Cardiac Efferent Innervation" by Randall et al., in Neurocardiology, edited by Kulbertus et al, Futura Publishing Co., 1988, direct surgical excision of the fat pad associated with the SA node affects the functioning of the SA node without significantly affecting the AV node. Similarly, excision of the fat pad associated with the AV node affects functioning of the AV node without significantly affecting the SA node.

As set forth in the article "Parasympathetic Postganglionic Pathways to the Sinoatrial Node," Bluemel et al., Am. J. Physiol. 259, (Heart Circ. Physiol. 28) H1504–H1510, 1990, stimulation of the fat pad associated with the SA node results in slowing of the sinus rate without the accompanying prolongation of AV conduction time which normally results from vagal nerve stimulation. The article also indicates that stimulation of the fat pad associated with the AV node is believed to produce corresponding effects limited to the AV node, i.e., extension of the AV conduction time without concurrent slowing of the sinus rate.

As set forth in the article "Neural Effects on Sinus Rate and Atrial Ventricular Conduction Produced by Electrical Stimulation From a Transvenous Electrode Catheter in the Canine Right Pulmonary Artery" by Cooper et al., published in Circulation Research, Vol. 46, No. 1, January, 1980, pp. 48–57, the fat pads associated with both the AV node and the. SA node may be stimulated by means of electrodes located in the right pulmonary artery. The results obtained include both a depression of the sinus rate and a prolongation of the AV conduction time in response to continuous stimulation at 2–80 Hz at up to 50 ma.

Generally in healthy individuals, the SA node functions as the pacemaker. Normal heart rhythm associated with the SA node is typically referred to as sinus rhythm. When the SA node fails, the AV node generally takes over creating a heart rate of approximately 35 to 60 beats per minute. Heart rhythm associated with the AV node is typically referred to as nodal rhythm. When the AV node itself is blocked or injured, a new even slower pacemaker site may form at the junction of the AV node and the His bundle. Heart rhythm associated with this junction is typically referred to as junctional escape rhythm. When this junction site is inhibited, the Purkinje fibers in the His bundle or below may act as a pacemaker creating a heart rate of approximately 30 beats per minute. Heart rhythm associated with the Purkinje fibers is typically referred to as idioventricular rhythm.

In one embodiment of the present invention, nerve stimulator 210 may be used to electrically manipulate cardiac rhythm by stimulating the carotid sinus nerve, the fat pad associated with the SA node, the fat pad associated with the AV node, the junction of the AV node and the His bundle and/or the Purkinje fibers.

In one embodiment of the present invention, nerve stimulator 210 is used alone or in combination with other heart rate inhibiting agents to temporarily stop or slow the beating heart, thereby eliminating or reducing heart motion and/or blood flow during a medical procedure. For example, the present invention may be used to eliminate or reduce motion in the anastomosis field during CABG procedures such that a facilitated anastomosis procedure may be performed safely and effectively. The number of occasions that the vagal nerve may be stimulated depends on the type of medical procedure to be performed. Likewise, the type of medical procedure to be performed will dictate the duration of the individual electrical stimulations.

Nerve stimulator 210 may be powered by AC current, DC current or it may be battery powered either by a disposable or re-chargeable battery. Nerve stimulator 210 may be configured to synchronize activation and deactivation of breathing regulator 240 with vagal stimulation, thereby minimizing or eliminating unwanted heart and chest motion associated with the patient's breathing. Nerve stimulator 210 may comprise a surgeon controlled switch box. A switch may be incorporated in or on one of the surgeon's instruments, such as surgical site retractor, or any other location easily and quickly accessed by the surgeon for regulation of the nerve stimulator 210 by the surgeon. The switch may be, for example, a hand switch, a foot switch, or a voice-activated switch comprising voice-recognition technologies.

A visual and/or audible signal used to alert a surgeon to the completion or resumption of vagal nerve stimulation may be incorporated into nerve stimulator 210. For example, a beeping tone or flashing light that increases in frequency as the nerve stimulation period should end or begin may be used.

Nerve stimulator 210 may be slaved to cardiac stimulator 220 or cardiac stimulator 220 may be slaved to nerve stimulator 210. For example, the output of cardiac stimulator 220 may be off whenever the output of nerve stimulator 210 is on. Software controlling cardiac stimulator 220 may be designed to automatically commence cardiac pacing if the heart does not resume beating within a pre-determined interval after cessation of vagal nerve stimulation. In addition, the software controlling nerve stimulator 210 may be designed to automatically stop vagal nerve stimulation if the heart has been stopped for too long.

In one embodiment of system 200, nerve stimulator 210 may be one or more electrodes. Electrodes used to stimulate a nerve such as the vagal nerve may be, for example, non-invasive, e.g., clips, or invasive, e.g., needles or probes. The application of an electrical stimulus to the right or left vagal nerve may include, but is not limited to bipolar and/or monopolar techniques. Different electrode positions are accessible through various access openings, for example, in the cervical or thorax regions. Nerve stimulation electrodes 210 may be positioned through a thoracotomy, sternotomy, endoscopically through a percutaneous port, through a stab wound or puncture, through a small incision in the neck or chest, through the internal jugular vein, the esophagus, the trachea, placed on the skin or in combinations thereof. Electrical stimulation may be carried out on the right vagal nerve, the left vagal nerve or to both nerves simultaneously or sequentially. The present invention may include various electrodes, catheters and electrode catheters suitable for vagal nerve stimulation to temporarily stop or slow the beating heart alone or in combination with other heart rate inhibiting agents.

Nerve stimulation electrodes 210 may be endotracheal, endoesophageal, intravascular, transcutaneous, intracutaneous, patch-type, balloon-type, cuff-type, basket-type, umbrella-type, tape-type, screw-type, barb-type, metal, wire or suction-type electrodes. Guided or steerable catheter devices comprising electrodes may be used alone or in combination with the nerve stimulation electrodes 210. For example, a catheter comprising one or more wire, metal strips or metal foil electrodes or electrode arrays may be inserted into the internal jugular vein to make electrical contact with the wall of the internal jugular vein, and thus stimulate the vagal nerve adjacent to the internal jugular vein. Access to the internal jugular vein may be via, for example, the right atrium, the right atrial appendage, the inferior vena cava or the superior vena cava. The catheter may comprise, for example, a balloon, which may be inflated with air or liquid to press the electrodes firmly against the vessel wall. Similar techniques may be performed by insertion of a catheter-type device into the trachea or esophagus. Additionally, tracheal tubes and esophageal tubes comprising electrodes may be used.

Nerve stimulation electrodes 210 may be oriented in any fashion along the catheter device, including longitudinally or transversely. Various techniques such as ultrasound, fluoroscopy and echocardiography may be used to facilitate positioning of the electrodes. If desired or necessary, avoidance of obstruction of blood flow may be achieved with notched catheter designs or with catheters that incorporate one or more tunnels or passageways.

In one embodiment of the present invention, the location of the electrodes 210 is chosen to elicit maximum bradycardia effectiveness while minimizing current spread to adjacent tissues and vessels and to prevent the induction of post stimulation tachycardia. Furthermore, a non-conductive material such as plastic may be employed to sufficiently enclose the electrodes of all the configurations to shield them from the surrounding tissues and vessels, while exposing their confronting edges and surfaces for positive contact with the vagal nerve or selected tissues.

System 200 may also include cardiac stimulator 220, which may be used to stimulate the heart as desired. As with nerve stimulator 210, cardiac stimulator 220 may be intermittently stopped and started to allow the surgeon to perform individual steps of a medical procedure.

Cardiac stimulator 220 may be a conventional ventricular demand pacer or dual chamber (atrial-ventricular) pacer. Cardiac stimulator 220 may be powered by AC current, DC current or it may be battery powered either by a disposable or re-chargeable battery. Cardiac stimulator 220 may be configured to synchronize activation and deactivation of breathing regulator 240 with pacing, thereby minimizing or eliminating unwanted heart and chest motion associated with the patient's breathing. Cardiac stimulator 220 may be any conventional pacing device suitable for ventricular demand pacing and having leads electrically coupled to a switch box. Cardiac stimulator 220 may be combined in a single unit with a switch box. Cardiac stimulator 220 may comprise a surgeon controlled switch box. A switch may be incorporated in or on one of the surgeon's instruments, such as surgical site retractor, or any other location easily and quickly accessed by the surgeon for regulation of the cardiac stimulator by the surgeon. The switch may be, for example, a hand switch, a foot switch, or a voice-activated switch comprising voice-recognition technologies. A single switch may be used to regulate both cardiac stimulator 220 and nerve stimulator 210.

A visual and/or audible signal used to prepare a surgeon for the resumption of pacing may be incorporated into cardiac stimulator 220. For example, a beeping tone or flashing light that increases in frequency as the pacing period ends may be used. A single signaling method or device may be used for both cardiac stimulator 220 and nerve stimulator 210.

In one embodiment of system 200 cardiac stimulator may be one or more electrodes. Cardiac electrodes 220 used to stimulate the heart may be, for example, non-invasive, e.g., clips, or invasive, e.g., needles or probes. Electrodes 220 may be positioned through a thoracotomy, sternotomy, endoscopically through a percutaneous port, through a stab wound or puncture, through a small incision in the chest, placed on the chest or in combinations thereof. The present invention may also use various electrodes, catheters and electrode catheters suitable for pacing the heart, e.g., epicardial, patch-type, intravascular, balloon-type, basket-type, umbrella-type, tape-type electrodes, suction-type, pacing electrodes, endotracheal electrodes, endoesophageal electrodes, transcutaneous electrodes, intracutaneous electrodes, screw-type electrodes, barb-type electrodes, bipolar electrodes, monopolar electrodes, metal electrodes, wire electrodes and cuff electrodes. Guided or steerable catheter devices comprising electrodes may be used alone or in combination with the electrodes.

Compression system 204, nerve stimulator 210 and/or cardiac stimulator 220 may be slaved to a robotic system or a robotic system may be slaved to compression system 204, nerve stimulator 210 and/or cardiac stimulator 220. Breathing regulator 240 and other components may also be slaved to such a system. Computer and voice-controlled robotic systems that position and maneuver endoscopes and/or other surgical instruments for performing microsurgical procedures such as anastomoses through small incisions may be used by a surgeon to perform precise and delicate maneuvers. These robotic systems may allow a surgeon to perform a variety of microsurgical procedures including endoscopic CABG. Endoscopic CABG may allow multiple occluded coronary arteries to be bypassed without a thoracotomy or mini-thoracotomy. Heart valve repair and replacement may also be other surgical applications for these robotic systems. In general, robotic systems may include head-mounted displays that integrate 3-D visualization of surgical anatomy and related diagnostic and monitoring data, miniature high-resolution 2-D and 3-D digital cameras, a computer, a high power light source and a standard video monitor.

System 200 may also include a breathing regulator 240. In one embodiment, the breathing regulator 240 may be used to stimulate the phrenic nerve in order to provide a diaphragmatic pacemaker. Breathing regulator 240 may comprise one or more electrodes for supplying electrical current to the phrenic nerve to control breathing during vagal and/or cardiac stimulation and/or destimulation. Electrodes used to stimulate the phrenic nerve may be, for example, non-invasive, e.g., clips, or invasive, e.g., needles or probes. The application of an electrical stimulus to the phrenic nerve may include, but is not limited to bipolar and/or monopolar techniques. Different electrode positions are accessible through various access openings, for example, in the cervical or thorax regions. Nerve stimulation electrodes may be positioned through a thoracotomy, sternotomy, endoscopically through a percutaneous port, through a stab wound or puncture, through a small incision, placed on the skin or in combinations thereof. The present invention may include various electrodes, catheters and electrode catheters suitable for phrenic nerve stimulation to control breathing.

Phrenic nerve stimulation electrodes may be intravascular, patch-type, balloon-type, basket-type, umbrella-type, tape-type, cuff-type, suction-type, screw-type, barb-type, bipolar, monopolar, metal, wire, endotracheal, endoesophageal, intravascular, transcutaneous or intracutaneous electrodes. Guided or steerable catheter devices comprising electrodes may be used alone or in combination with the nerve stimulation electrodes. For example, a catheter comprising one or more wire, metal strips or metal foil electrodes or electrode arrays may be used. The catheter may comprise, for example, a balloon that may be inflated with air or liquid to press the electrodes firmly against a vessel wall that lays adjacent the phrenic nerve.

Phrenic nerve stimulation electrodes may be oriented in any fashion along the catheter device, including longitudinally or transversely. Various techniques such as ultrasound, fluoroscopy and echocardiography may be used to facilitate positioning of the electrodes. If desired or necessary, avoidance of obstruction of blood flow may be achieved with notched catheter designs or with catheters that incorporate one or more tunnels or passageways.

In another embodiment, the breathing regulator 240 may comprise a connector that interfaces with a patient's respirator, and sends a logic signal to activate or deactivate the respirator to control breathing during vagal and/or cardiac stimulation and/or destimulation.

System 200 may incorporate a controller as described above or any suitable processor 230. For example, the processor may process the sensed blood information from compression system 204. The controller may store or process such information as the state of compression of various limbs or the blood flow to or from various limbs. The controller may also store or process such information before a medical procedure and during the procedure.

Controller 230 may be used to gather information from nerve stimulation electrodes 210 and cardiac stimulation electrodes 220 or compression system 204. Controller 230 may also be used to control the stimulation levels and stimulation duration from nerve stimulation electrodes 210 and cardiac stimulation electrodes 220. Controller 230 may also be used to control compression levels and compression duration from compression system 204. This information may be used to adjust stimulation levels and stimulation times from nerve stimulation electrodes 210 and cardiac stimulation electrodes 220. This information may also be used to adjust compression levels and compression times of compression system 204.

Figure 3:
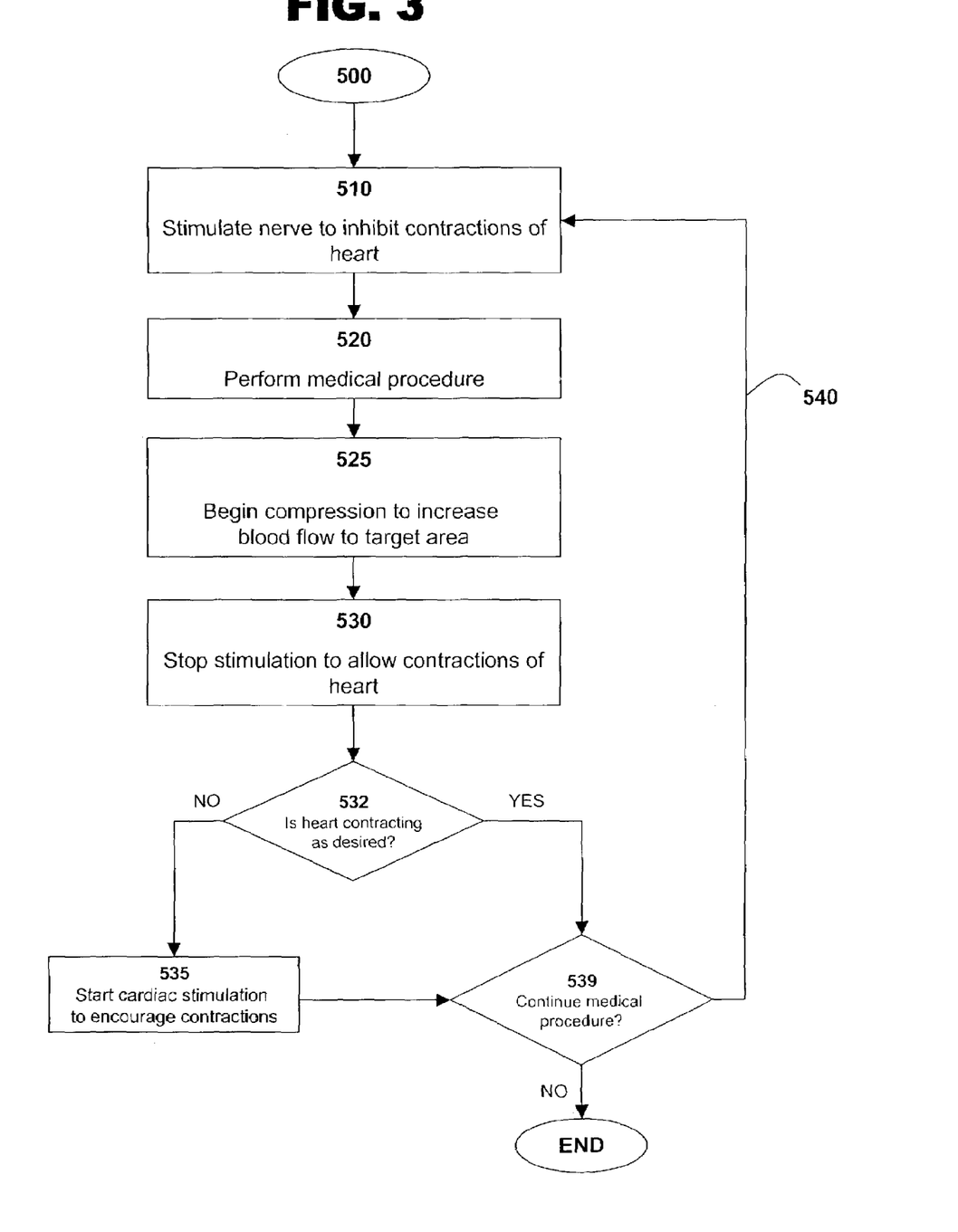
FIG. 3 is a flow diagram of one embodiment of a method of performing a medical procedure in accordance with the present invention.

FIG. 3 shows a flow diagram of one embodiment of the present invention. The patient is prepared for a medical procedure at 500.

At Block 510, a nerve that controls the beating of the heart is stimulated. Such a nerve may be for example a vagal nerve. At Block 510, one or more of a variety of pharmacological agents or drugs may be delivered. These drugs may produce reversible asystole of a heart while maintaining the ability of the heart to be electrically paced.

A variety of pharmacological agents or drugs may also be delivered at other times during the procedure 500. These drugs may also produce reversible asystole of a heart while maintaining the ability of the heart to be electrically paced. Other drugs may be administered for a variety of functions and purposes as described below. Drugs may be delivered at any appropriate time during the medical procedure, for example, at the beginning of the procedure, intermittently during the procedure, continuously during the procedure or following the procedure.

Drugs, drug formulations or compositions suitable for administration to a patient during a medical procedure may include a pharmaceutically acceptable carrier or solution in an appropriate dosage. There are a number of pharmaceutically acceptable carriers that may be used for delivery of various drugs, for example, via direct injection, oral delivery, suppository delivery, transdermal delivery, epicardial delivery and/or inhalation delivery. Pharmaceutically acceptable carriers include a number of solutions, preferably sterile, for example, water, saline, Ringer's solution and/or sugar solutions such as dextrose in water or saline. Other possible carriers that may be used include sodium citrate, citric acid, amino acids, lactate, mannitol, maltose, glycerol, sucrose, ammonium chloride, sodium chloride, potassium chloride, calcium chloride, sodium lactate, and/or sodium bicarbonate. Carrier solutions may or may not be buffered.

Drug formulations or compositions may include antioxidants or preservatives such as ascorbic acid. They may also be in a pharmaceutically acceptable form for parenteral administration, for example to the cardiovascular system, or directly to the heart, such as intracoronary infusion or injection. Drug formulations or compositions may comprise agents that provide a synergistic effect when administered together. A synergistic effect between two or more drugs or agents may reduce the amount that normally is required for therapeutic delivery of an individual drug or agent. Two or more drugs may be administered, for example, sequentially or simultaneously. Drugs may be administered via one or more bolus injections and/or infusions or combinations thereof. The injections and/or infusions may be continuous or intermittent. Drugs may be administered, for example, systemically or locally, for example, to the heart, to a coronary artery and/or vein, to a pulmonary artery and/or vein, to the right atrium and/or ventricle, to the left atrium and/or ventricle, to the aorta, to the AV node, to the SA node, to a nerve and/or to the coronary sinus. Drugs may be administered or delivered via intravenous, intracoronary and/or intraventricular administration in a suitable carrier. Examples of arteries that may be used to deliver drugs to the AV node include the AV node artery, the right coronary artery, the right descending coronary artery, the left coronary artery, the left anterior descending coronary artery and Kugel's artery. Drugs may be delivered systemically, for example, via oral, transdermal, intranasal, suppository or inhalation methods. Drugs also may be delivered via a pill, a spray, a cream, an ointment or a medicament formulation.

Drugs may be delivered via a drug delivery device that may comprise a catheter, such as a drug delivery catheter or a guide catheter, a patch, such as a transepicardial patch that slowly releases drugs directly into the myocardium, a cannula, a pump and/or a hypodermic needle and syringe assembly. A drug delivery catheter may include an expandable member, e.g., a low-pressure balloon, and a shaft having a distal portion, wherein the expandable member is disposed along the distal portion. A catheter for drug delivery may comprise one or more lumens and may be delivered endovascularly via insertion into a blood vessel, e.g., an artery such as a femoral, radial, subclavian or coronary artery. The catheter can be guided into a desired position using various guidance techniques, e.g., flouroscopic guidance and/or a guiding catheter or guide wire techniques.

Drugs may be delivered via an iontophoretic drug delivery device placed on the heart. In general, the delivery of ionized drugs may be enhanced via a small current applied across two electrodes. Positive ions may be introduced into the tissues from the positive pole, or negative ions from the negative pole. The use of iontophoresis may markedly facilitate the transport of certain ionized drug molecules. For example, lidocaine hydrochloride may be applied to the heart via a drug patch comprising the drug. A positive electrode could be placed over the patch and current passed. The negative electrode would contact the heart or other body part at some desired distance point to complete the circuit. One or more of the electrodes may also be used as nerve stimulation electrodes 210 or as cardiac stimulation electrodes 220.

The two divisions of the autonomic nervous system that regulate the heart have opposite functions. First, the adrenergic or sympathetic nervous system increases heart rate by releasing epinephrine and norepinephrine. Second, the parasympathetic system also known as the cholinergic nervous system or the vagal nervous system decreases heart rate by releasing acetylcholine. Catecholamines such as norepinephrine (also called noradrenaline) and epinephrine (also called adrenaline) are agonists for beta-adrenergic receptors. An agonist is a stimulant biomolecule or agent that binds to a receptor.

Beta-adrenergic receptor blocking agents compete with beta-adrenergic receptor stimulating agents for available beta-receptor sites. When access to beta-receptor sites are blocked by receptor blocking agents, also known as beta-adrenergic blockade, the chronotropic or heart rate, inotropic or contractility, and vasodilator responses to receptor stimulating agents are decreased proportionately. Therefore, beta-adrenergic receptor blocking agents are agents that are capable of blocking beta-adrenergic receptor sites.

Since beta-adrenergic receptors are concerned with contractility and heart rate, stimulation of beta-adrenergic receptors, in general, increases heart rate, the contractility of the heart and the rate of conduction of electrical impulses through the AV node and the conduction system.

Drugs, drug formulations and/or drug compositions that may be used according to this invention may include any naturally occurring or chemically synthesized (synthetic analogues) beta-adrenergic receptor blocking agents. Beta-adrenergic receptor blocking agents or □-adrenergic blocking agents are also known as beta-blockers or □-blockers and as class II antiarrhythmics.

The term "beta-blocker" appearing herein may refer to one or more agents that antagonize the effects of beta-stimulating catecholamines by blocking the catecholamines from binding to the beta-receptors. Examples of beta-blockers include, but are not limited to, acebutolol, alprenolol, atenolol, betantolol, betaxolol, bevantolol, bisoprolol, carterolol, celiprolol, chlorthalidone, esmolol, labetalol, metoprolol, nadolol, penbutolol, pindolol, propranolol, oxprenolol, sotalol, teratolo, timolol and combinations, mixtures and/or salts thereof.

The effects of administered beta-blockers may be reversed by administration of beta-receptor agonists, e.g., dobutamine or isoproterenol.

The parasympathetic or cholinergic system participates in control of heart rate via the sinoatrial (SA) node, where it reduces heart rate. Other cholinergic effects include inhibition of the AV node and an inhibitory effect on contractile force. The cholinergic system acts through the vagal nerve to release acetylcholine, which, in turn, stimulates cholinergic receptors. Cholinergic receptors are also known as muscarinic receptors. Stimulation of the cholinergic receptors decreases the formation of cAMP. Stimulation of cholinergic receptors generally has an opposite effect on heart rate compared to stimulation of beta-adrenergic receptors. For example, beta-adrenergic stimulation increases heart rate, whereas cholinergic stimulation decreases it. When vagal tone is high and adrenergic tone is low, there is a marked slowing of the heart (sinus bradycardia). Acetylcholine effectively reduces the amplitude, rate of increase and duration of the SA node action potential. During vagal nerve stimulation, the SA node does not arrest. Rather, pacemaker function may shift to cells that fire at a slower rate. In addition, acetylcholine may help open certain potassium channels thereby creating an outward flow of potassium ions and hyperpolarization. Acetylcholine also slows conduction through the AV node.

Drugs, drug formulations and/or drug compositions that may be used according to this invention may include any naturally occurring or chemically synthesized (synthetic analogues) cholinergic agent. The term "cholinergic agent" appearing herein may refer to one or more cholinergic receptor modulators or agonists. Examples of cholinergic agents include, but are not limited to, acetylcholine, carbachol (carbamyl choline chloride), bethanechol, methacholine, arecoline, norarecoline and combinations, mixtures and/or salts thereof.

Drugs, drug formulations and/or drug compositions that may be used according to this invention may include any naturally occurring or chemically synthesized cholinesterase inhibitor. The term "cholinesterase inhibitor" appearing herein may refer to one or more agents that prolong the action of acetylcholine by inhibiting its destruction or hydrolysis by cholinesterase. Cholinesterase inhibitors are also known as acetylcholinesterase inhibitors. Examples of cholinesterase inhibitors include, but are not limited to, edrophonium, neostigmine, neostigmine methylsulfate, pyridostigmine, tacrine and combinations, mixtures and/or salts thereof.

There are ion-selective channels within certain cell membranes. These ion selective channels include calcium channels, sodium channels and/or potassium channels. Therefore, other drugs, drug formulations and/or drug compositions that may be used according to this invention may include any naturally occurring or chemically synthesized calcium channel blocker. Calcium channel blockers inhibit the inward flux of calcium ions across cell membranes of arterial smooth muscle cells and myocardial cells. Therefore, the term "calcium channel blocker" appearing herein may refer to one or more agents that inhibit or block the flow of calcium ions across a cell membrane. The calcium channel is generally concerned with the triggering of the contractile cycle. Calcium channel blockers are also known as calcium ion influx inhibitors, slow channel blockers, calcium ion antagonists, calcium channel antagonist drugs and as class IV antiarrhythmics. A commonly used calcium channel blocker is verapamil.

Administration of a calcium channel blocker, e.g., verapamil, generally prolongs the effective refractory period within the AV node and slows AV conduction in a rate-related manner, since the electrical activity through the AV node depends significantly upon the influx of calcium ions through the slow channel. A calcium channel blocker has the ability to slow a patient's heart rate, as well as produce AV block. Examples of calcium channel blockers include, but are not limited to, amiloride, amlodipine, bepridil, diltiazem, felodipine, isradipine, mibefradil, nicardipine, nifedipine (dihydropyridines), nickel, nimodinpine, nisoldipine, nitric oxide (NO), norverapamil and verapamil and combinations, mixtures and/or salts thereof. Verapamil and diltiazem are very effective at inhibiting the AV node, whereas drugs of the nifedipine family have a lesser inhibitory effect on the AV node. Nitric oxide (NO) indirectly promotes calcium channel closure. NO may be used to inhibit contraction. NO may also be used to inhibit sympathetic outflow, lessen the release of norepinephrine, cause vasodilation, decrease heart rate and decrease contractility. In the SA node, cholinergic stimulation leads to formation of NO.

Other drugs, drug formulations and/or drug compositions that may be used according to this invention may include any naturally occurring or chemically synthesized sodium channel blocker. Sodium channel blockers are also known as sodium channel inhibitors, sodium channel blocking agents, rapid channel blockers or rapid channel inhibitors. Antiarrhythmic agents that inhibit or block the sodium channel are known as class I antiarrhythmics, examples include, but are not limited to, quinidine and quinidine-like agents, lidocaine and lidocaine-like agents, tetrodotoxin, encainide, flecainide and combinations, mixtures and/or salts thereof. Therefore, the term "sodium channel blocker" appearing herein may refer to one or more agents that inhibit or block the flow of sodium ions across a cell membrane or remove the potential difference across a cell membrane. For example, the sodium channel may also be totally inhibited by increasing the extracellular potassium levels to depolarizing hyperkalemic values, which remove the potential difference across the cell membrane. The result is inhibition of cardiac contraction with cardiac arrest (cardioplegia). The opening of the sodium channel (influx of sodium) is for swift conduction of the electrical impulse throughout the heart.

Other drugs, drug formulations and/or drug compositions that may be used according to this invention may include any naturally occurring or chemically synthesized potassium channel agent. The term "potassium channel agent" appearing herein may refer to one or more agents that impact the flow of potassium ions across the cell membrane. There are two major types of potassium channels. The first type of channel is voltage-gated and the second type is ligand-gated. Acetylcholine-activated potassium channels, which are ligand-gated channels, open in response to vagal stimulation and the release of acetylcholine. Opening of the potassium channel causes hyperpolarization, which decreases the rate at which the activation threshold is reached. Adenosine is one example of a potassium channel opener. Adenosine slows conduction through the AV node. Adenosine, a breakdown product of adenosine triphosphate, inhibits the AV node and atria. In atrial tissue, adenosine causes the shortening of the action potential duration and causes hyperpolarization. In the AV node, adenosine has similar effects and also decreases the action potential amplitude and the rate of increase of the action potential. Adenosine is also a direct vasodilator by its actions on the adenosine receptor on vascular smooth muscle cells. In addition, adenosine acts as a negative neuromodulator, thereby inhibiting release of norepinephrine. Class III antiarrhythmic agents also known as potassium channel inhibitors lengthen the action potential duration and refractoriness by blocking the outward potassium channel to prolong the action potential. Amiodarone and d-sotalol are both examples of class III antiarrhythmic agents.

Potassium is the most common component in cardioplegic solutions. High extracellular potassium levels reduce the membrane resting potential. Opening of the sodium channel, which normally allows rapid sodium influx during the upstroke of the action potential, is therefore inactivated because of a reduction in the membrane resting potential. The present invention may be combined with conventional CPB, the induced asystole as described by this invention may serve as a substitute for conventional cardioplegic arrest. For example, the combination of drugs and vagal stimulation may be used as a cardioplegic agent in a variety of medical procedures.

Drugs, drug formulations and/or drug compositions that may be used according to this invention may comprise one or more of any naturally occurring or chemically synthesized beta-blocker, cholinergic agent, cholinesterase inhibitor, calcium channel blocker, sodium channel blocker, potassium channel agent, adenosine, adenosine receptor agonist, adenosine deaminase inhibitor, dipyridamole, monoamine oxidase inhibitor, digoxin, digitalis, lignocaine, bradykinin agents, serotoninergic agonist, antiarrythmic agents, cardiac glycosides, local anesthetics and combinations or mixtures thereof. Digitalis and digoxin both inhibit the sodium pump. Digitalis is a natural inotrope derived from plant material, while digoxin is a synthesized inotrope. Dipyridamole inhibits adenosine deaminase, which breaks down adenosine. Drugs, drug formulations and/or drug compositions capable of reversibly suppressing autonomous electrical conduction at the SA and/or AV node, while still allowing the heart to be electrically paced to maintain cardiac output may be used according to this invention.

In one embodiment, the cardiac asystole produced in accordance with the present invention is reversible, e.g., chemically such as by the administration of atropine or by natural forces. Beta-adrenergic stimulation or administration of calcium solutions may be used to reverse the effects of a calcium channel blocker such as verapamil. Agents that promote heart rate and/or contraction may be used in a preferred embodiment of the present invention. For example, dopamine, a natural catecholamine, is known to increase contractility. Positive inotropes are agents that specifically increase the force of contraction of the heart. Glucagon, a naturally occurring hormone, is known to increase heart rate and contractility. Glucagon may be used to reverse the effects of a beta-blocker since its effects bypass the beta-receptor. Forskolin is known to increase heart rate and contractility. As mentioned earlier, epinephrine and norepinephrine naturally increase heart rate and contractility. Thyroid hormone, phosphodiesterase inhibitors and prostacyclin, a prostaglandin, are also known to increase heart rate and contractility. In addition, methylxanthines are known to prevent adenosine from interacting with its cell receptors.

Typically, vagal nerve stimulation prevents the heart from contracting. This non-contraction must then be followed by periods without vagal nerve stimulation during which the heart is allowed to contract, and blood flow is restored throughout the body. During the time that the nerve stimulation is preventing contraction of the heart, all or a portion of the medical procedure may be carried out or begun (Block 520). Such a procedure may be for example surgery on the heart. Alternatively, the procedure may be surgery performed on another organ of the body. At Block 520, one or more of a variety of pharmacological agents or drugs may be delivered or may continue to be delivered. These drugs may produce reversible asystole of a heart while maintaining the ability of the heart to be electrically paced. Other drugs may be administered for a variety of functions and purposes as described above.

The term "medical procedure" may mean any one or more medical or surgical procedures such as, for example cardiac surgery, performed with or without cardiopulmonary bypass (CPB) circuits, heart valve repair, heart valve replacement, MAZE procedures, revascularization procedures, percutaneous myocardial revascularization (PMR) procedures, transmyocardial revascularization (TMR), CABG procedures, anastomosis procedures, non-surgical procedures, fluoroscopic procedures, beating heart surgery, vascular surgery, neurosurgery, brain surgery, electrophysiology procedures, diagnostic and therapeutic procedures, ablation procedures, ablation of arrhythmias, endovascular procedures, treatment of the liver, spleen, heart, lungs, and major blood vessels, aneurysm repair, imaging procedures of the heart and great vessels, CAT scans or MRI procedures, pharmacological therapies, drug delivery procedures, gene therapies, cellular therapies, cancer therapies, radiation therapies, genetic, cellular, tissue and/or organ manipulation or transplantation procedures, coronary angioplasty procedures, placement or delivery of coated or noncoated stents, atherectomy procedures, atherosclerotic plaque manipulation and/or removal procedures, procedures where bleeding needs to be precisely controlled, procedures that require precise control of cardiac motion and/or bleeding.

When the medical procedure comprises one or more medical devices, e.g., coated stents, these devices may be coated with one or more radioactive materials and/or biological agents such as, for example, an anticoagulant agent, an antithrombotic agent, a clotting agent, a platelet agent, an anti-inflammatory agent, an antibody, an antigen, an immunoglobulin, a defense agent, an enzyme, a hormone, a growth factor, a neurotransmitter, a cytokine, a blood agent, a regulatory agent, a transport agent, a fibrous agent, a protein, a peptide, a proteoglycan, a toxin, an antibiotic agent, an antibacterial agent, an antimicrobial agent, a bacterial agent or component, hyaluronic acid, a polysaccharide, a carbohydrate, a fatty acid, a catalyst, a drug, a vitamin, a DNA segment, a RNA segment, a nucleic acid, a lectin, an antiviral agent, a viral agent or component, a genetic agent, a ligand and a dye (which acts as a biological ligand). Biological agents may be found in nature (naturally occurring) or may be chemically synthesized.

The medical procedure may be non-invasive, minimally invasive and/or invasive. The medical procedure may entail a port-access approach, a partially or totally endoscopic approach, a sternotomy approach or a thoracotomy approach. The medical procedure may include the use of various mechanical stabilization devices or techniques as well as various robotic or imaging systems.

In one method, the heart may be temporarily slowed or intermittently stopped for short periods of time to permit the surgeon to accomplish the required surgical task and yet still allow the heart itself to supply blood circulation to the body. For example, stimulation of the vagus nerve in order to temporarily and intermittently slow or stop the heart is described in U.S. Pat. No. 6,006,134 entitled "Method and Device for Electronically Controlling the Beating of a Heart Using Venous Electrical Stimulation of Nerve Fibers," Dec. 21, 1999, to inventors Hill and Junkman. This patent is assigned to Medtronic, Inc. and is incorporated herein by reference.

During this medical procedure, cardiac contractions are stopped or slowed. After a period of time, the heart may be allowed to contract so that blood may flow to the brain and other areas that require oxygen. In order to direct blood flow to a desired area, one or more components of the patient's body may be compressed using compression system 100, 204 (Block 525). Typically, it is most desirable that the blood flow to the brain. Thus, one or more limbs may be compressed to direct blood flow first to the brain.

Once compression has been started to appropriately direct blood flow, the heart may be allowed to contract (Block 530). Cardiac contractions may need to occur intermittently during the procedure to ensure adequate blood flow. In one embodiment, the stimulation from the nerve stimulator 210 is stopped or slowed enough to allow the heart to contract. For example, the vagal nerve stimulation is removed, thereby allowing cardiac contractions to occur.

At Block 532, it may be determined whether the heart is contracting as desired. If not, cardiac stimulation may also be used to encourage contractions (Block 535). For example, cardiac stimulator 220 may be used to stimulation contractions of the heart.

Once the heart contracts, blood will flow as directed by the compression. For example, compression of one or more limbs will direct blood flow to the brain first.

Output regarding compression from compression system 100, 204 may be communicated to the surgeon by a number of suitable means. For example, the output may be indicated on a display or monitor on control unit 14. A visual or audio signal may indicate when compression reaches a certain level, which portions of the body are being compressed, the level of blood flowing to various areas or which areas are receiving blood flow.

Additionally, the amount of compression used may be adjusted based on the output of the system 100, 204. For example, the level of compression may be increased or decreased based on output about where blood is flowing. This adjustment may be automatic or may be controlled by the surgeon.

The present invention permits the heart to be stilled or quiescent for selected and controllable periods of time in order to permit cardiac or other surgery to be performed. While such a period of quiescence is desired, it must not last too long, otherwise insufficient blood and oxygen is delivered to organs. Thus, it is necessary to have the periods when the heart is beating (Blocks 530, 535). At Blocks 530, 535, one or more of a variety of pharmacological agents or drugs may be delivered or may continue to be delivered. These drugs may produce reversible asystole of a heart while maintaining the ability of the heart to be electrically paced. Particularly at Block 535, drugs may be administered to encourage heart contractions. Other drugs may be administered for a variety of functions and purposes as described above At 539, it may be determined if additional medical procedures or additional stages of medical procedures need to be performed. If so, the heart may again be stilled using the methods of stilling the heart described above. The method may then be repeated (as in the loop designated by 540). For example, the heart may again be prevented from contracting by stimulation of the vagal nerve (510). Additional drugs may be delivered or the drugs previously administered may continue to be administered.

At this time, compression may be stopped until the step designated by Block 525 is reached again. Alternatively, once compression is begun, compression may continue until the medical procedure has finished.

This cycle may be repeated until the procedure, such as the surgery, is completed. As the cycle continues, compression system 100, 204 may be used to direct the flow of blood appropriately.

For example, a surgical procedure at 520 may require several stitches to be made by the surgeon. The surgeon may stimulate the vagal nerve at 510 to stop the heart. Then the surgeon may make the first stitch at 520. The surgeon may then reduce or halt stimulation at 530 and allow the heart to contract. The surgeon may then compress appropriate portions of the body to direct blood flow. Then at 540, the surgeon may return to 510 to inhibit contractions of the heart. At 520, the surgeon will then make the second stitch. This process may be repeated (the loop designated by 540 may be repeated) until all the required stitches have been made. Meanwhile, compression is used when appropriate to direct the flow of blood.

In one embodiment, after the procedure is completed, step 535 is performed until the heart is beating normally. Once it has been determined at 532 that the medical procedure is complete, the surgeon may continue stimulating the heart until satisfied that the heart is beating normally. Additionally, compression system 100, 204 may be used to direct the flow of blood until blood flow is sufficient in all areas of the body. For example, compression system 100, 204 may compress one or more limbs to direct blood flow to the brain first. Then compression system may compress only the legs to direct blood flow to the upper part of the patient's body next. Then compression system may stop compression of the legs so that blood may flow to the lower portion of the patient's body. At the procedure's end, one or more of a variety of pharmacological agents or drugs may be delivered or may continue to be delivered to alleviate pain or aid in recuperation. Other drugs may be administered for a variety of functions and purposes as described above.

Figure 4:
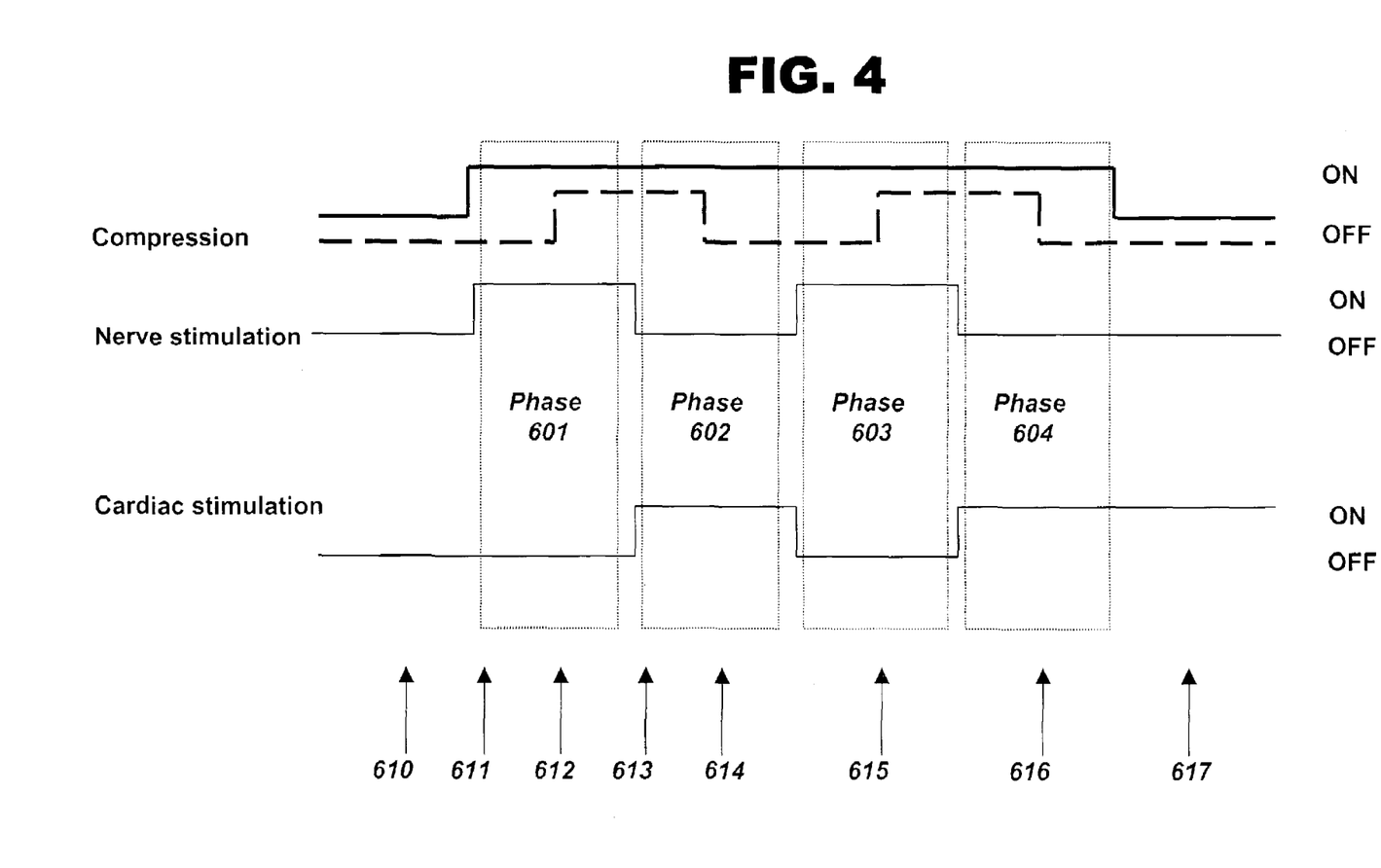
FIG. 4 is a timeline view of one embodiment of a system for directing blood flow during a medical procedure in accordance with the present invention.

FIG. 4 is a timeline illustrating a relationship between a compression system, a nerve stimulator and a cardiac stimulator.

Point 610 indicates a point before the medical procedure has begun. At this point 610, both nerve stimulation and cardiac stimulation are off. At point 610, the heart is beating regularly. Compression system 100, 204 may be off.

Then nerve stimulation is turned on to inhibit beating of the heart. During phase 601, the vagal nerve stimulation is on and the cardiac stimulation is off. This is the condition of the two types of stimulation at step 520 described above. In one embodiment, as shown by the solid compression line of FIG. 4, compression of one or more body components may be turned on at phase 601 and may continue during the procedure. Alternatively, as shown by the dotted compression line of FIG. 4, compression may be coordinated to turn on and off in relation to nerve stimulation and cardiac stimulation as discussed further below.

Point 611 is a representative point during phase 601. At point 611, the contractions of the heart are stilled or substantially slowed. Also, at point 611, compression of one or more body components may occur. Alternatively, compression may not occur until a point as represented by point 612. At point 612, compression is turned on in anticipation of cardiac stimulation. The surgeon may finish the step of the procedure occurring during phase 601 while compression begins and then proceed to phase 602.

During phase 602 the vagal stimulation is turned off (as described at step 530) and the cardiac stimulation may be turned on (as described at 535). Point 613 is a representative point during phase 602. At point 613, the contractions are allowed and/or may be induced. In one embodiment, compression occurring at point 613 directs blood flow appropriately as described above. For example, the compression may direct blood flow to the brain. Compression may then be turned off, for example at a point represented by point 614. Then, phase 602 ends with cardiac stimulation ending and nerve stimulation beginning again in order to stop contractions of the heart.

During phase 603, the vagal nerve stimulation is again turned on and the cardiac stimulation is turned off. In one embodiment as indicated by the solid compression line, compression system 100, 204 has been operating throughout each phase and continues to operate through phase 603. The amount or duration of vagal stimulation during phase 603 may be the same or different than the amount or duration of vagal stimulation during phase 601. During phase 603 compression may again be turned on in (represented by point 615) in anticipation of cardiac contractions occurring during phase 604. The surgeon may finish another step of the procedure in phase 603.

During phase 604 the vagal stimulation is again turned off and the cardiac stimulation may again be turned on. The amount or duration of cardiac stimulation during phase 604 may be the same or different than the amount or duration of cardiac stimulation during phase 602. Again, following the dotted compression line shown in FIG. 4, it can be seen that during phase 604, compression may appropriately direct the flow of blood. In one embodiment as indicated by the solid compression line, compression system 100, 204 has been operating throughout each phase and continues to operate through phase 604. In another embodiment, compression system 100, 204 may be turned off once blood flow has been directed (as indicated at point 616).

The method of the present invention may be repeated as necessary until a point is reached, represented by point 617, when the necessary medical procedures are completed. At this point 617, nerve stimulation is off although cardiac stimulation may be left on in order to pace the heart to its normal rhythm. At point 617, compression system 100, 204 may be turned off once blood is flowing appropriately to all organs. Alternatively, compression system 100, 204 may be used to direct the flow of blood until blood flow is sufficient in all areas of the body. For example, compression system 100, 204 may compress one or more limbs to direct blood flow to the brain first. Then compression system may compress only the legs to direct blood flow to the upper part of the patient's body next. Then compression system may stop compression of the legs so that blood may flow to the lower portion of the patient's body. It is contemplated that compression unit 4 may be left on the patient after the procedure for such purposes as maintaining stasis or keeping the patient covered or warm. Compression unit 4 may be used in such a manner even if control unit 14 has been detached from compression unit 4 or even if compression unit 4 is not actively compressing a body portion.

Compression of a body portion in relation to cardiac and nerve stimulation may be coordinated automatically, for example by controller 230. Alternatively, a surgeon may manually coordinate the cardiac and nerve stimulation in relation to compression.

It will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein.

We claim:

1. A system for controlling blood flow to a target area during a medical procedure comprising:
    at least one compression member to cover a body portion comprising at least one limb, the compression member including a vessel harvesting opening, wherein the vessel harvesting opening is positioned on the compression member so that a blood vessel of a limb may be harvested through the vessel harvesting opening;
    a means to sense intermittent cardiac asystole; and
    a control unit to activate compression of the compression member, wherein the control unit activates compression of the compression member in response to intermittent cardiac asystole.

2. The system of claim 1 wherein the blood vessel is a saphenous vein.

3. A system for controlling blood flow during a medical procedure comprising:
    at least one compression member to cover at least one limb portion, the compression member including a plurality of body limb openings;
    a means to sense intermittent cardiac asystole; and
    a control unit to activate compression of the compression member, wherein the control unit activates compression of the compression member in response to intermittent cardiac asystole.

4. The system of claim 3 wherein the compression member covers a limb of a patient selected from the group consisting of an arm and a leg.

5. The system of claim 3 wherein the medical procedure is selected from the group consisting of:
    a surgical procedure, a non-surgical procedure, a fluoroscopic procedure, a cardiac procedure, a vascular procedure, a neurosurgical procedure, an electrophysiological procedure, a diagnostic procedure, a therapeutic procedure, an ablation procedure, an endovascular procedure, a liver procedure, a spleen procedure, a pulmonary procedure, an aneurysm repair, an imaging procedure, a CAT scan procedure, a MRI procedure, a pharmacological therapy, a drug delivery procedure, a biological delivery procedure, a genetic therapy, a cellular therapy, a cancer therapy, a radiation therapy, a transplantation procedure, a coronary angioplasty procedure, a stent delivery procedure, an atherectomy procedure, a procedure that requires precise control of cardiac motion, a procedure that requires precise control of bleeding, a non-invasive procedure, a minimally invasive procedure, an invasive procedure, a port-access procedure, an endoscopic procedure, a sternotomy procedure, a thoracotomy procedure and a robotic procedure.

6. The system of claim 3 further comprising a cardiac stimulator to adjust the beating of the heart.

7. The system of claim 3 further comprising a nerve stimulator to adjust the beating of the heart.

8. A compression system for controlling blood flow during a medical procedure, comprising:
    at least one compression member to cover at least one limb, the compression member including a plurality of limb openings;
    a control unit coupled to the compression member to activate compression of the compression member, wherein the control unit activates compression of the compression member intermittently during the medical procedure; and
    a nerve stimulator in communication with the control unit, wherein the nerve stimulator stimulates a vagal nerve intermittently to adjust the beating of a heart, wherein the control unit activates compression of the compression member in response to vagal nerve stimulation.

9. The system of claim 8 wherein the compression member further comprises a vessel harvesting opening.

10. The system of claim 8 wherein the compression member covers a limb of a patient selected from the group consisting of an arm and a leg.

11. The system of claim 8 wherein the medical procedure is selected from the group consisting of:
    a surgical procedure, a non-surgical procedure, a fluoroscopic procedure, a cardiac procedure, a vascular procedure, a neurosurgical procedure, an electrophysiological procedure, a diagnostic procedure, a therapeutic procedure, an ablation procedure, an endovascular procedure, a liver procedure, a spleen procedure, a pulmonary procedure, an aneurysm repair, an imaging procedure, a CAT scan procedure, a MRI procedure, a pharmacological therapy, a drug delivery procedure, a biological delivery procedure, a genetic therapy, a cellular therapy, a cancer therapy, a radiation therapy, a transplantation procedure, a coronary angioplasty procedure, a stent delivery procedure, an atherectomy procedure, a procedure that requires precise control of cardiac motion, a procedure that requires precise control of bleeding, a non-invasive procedure, a minimally invasive procedure, an invasive procedure, a port-access procedure, an endoscopic procedure, a sternotomy procedure, a thoracotomy procedure and a robotic procedure.

12. The system of claim 8 wherein the nerve stimulator stimulates the vagal nerve to stop beating of the heart.

13. The system of claim 8 wherein the nerve stimulator comprises at least one electrode.

14. The system of claim 13 wherein the electrode is selected from the group consisting of:
nerve stimulation electrodes, endotracheal electrodes, endoesophageal electrodes, intravascular electrodes, transcutaneous electrodes, intracutaneous electrodes, balloon-type electrodes, basket-type electrodes, umbrella-type electrodes, tape-type electrodes, suction-type electrodes, screw-type electrodes, barb-type electrodes, bipolar electrodes, monopolar electrodes, metal electrodes, wire electrodes, patch electrodes, cuff electrodes, clip electrodes, needle electrodes and probe electrodes.

15. The system of claim 8 further comprising a cardiac stimulator in communication with the control unit to adjust the beating of the heart.

16. The system of claim 15 wherein the cardiac stimulator stimulates the heart in order to induce beating of the heart.

17. The system of claim 15 wherein the cardiac stimulator comprises at least one electrode.

18. The system of claim 17 wherein the electrode is selected from the group consisting of:
cardiac stimulation electrodes, clip electrodes, needle electrodes, probe electrodes, pacing electrodes, epicardial electrodes, patch electrodes, intravascular electrodes, balloon-type electrodes, basket-type electrodes, tape-type electrodes, umbrella-type electrodes, suction-type electrodes, endotracheal electrodes, endoesophageal electrodes, transcutaneous electrodes, intracutaneous electrodes, screw-type electrodes, barb-type electrodes, bipolar electrodes, monopolar electrodes, metal electrodes, wire electrodes and cuff electrodes.

19. A system for controlling blood flow to a target area during a medical procedure comprising:
at least one compression member to cover a body portion comprising at least one limb, the compression member including a vessel harvesting opening, wherein the vessel harvesting opening is positioned on the compression member so that a blood vessel of a limb may be harvested through the vessel harvesting opening;
a control unit to activate compression of the compression member, wherein the control unit activates compression of the compression member in synchronization with the beating of a heart; and
a nerve stimulator in communication with the control unit, wherein the nerve stimulator stimulates a vagal nerve to adjust the beating of the heart, wherein the control unit activates compression of the compression member in response to vagal nerve stimulation.

20. A compression system for controlling blood flow during a medical procedure, comprising:
at least one compression member to cover a leg portion, the compression member comprising a vessel harvesting opening for harvesting at least a portion of a saphenous vein from the leg portion;
a control unit coupled to the compression member to activate compression of the compression member, wherein the control unit activates compression of the compression member intermittently during the medical procedure; and
a nerve stimulator in communication with the control unit, wherein the nerve stimulator stimulates a vagal nerve intermittently to adjust the beating of a heart, wherein the control unit activates compression of the compression member in response to vagal nerve stimulation.

* * * * *